United States Patent
von Oepen et al.

(10) Patent No.: US 10,933,216 B2
(45) Date of Patent: Mar. 2, 2021

(54) MULTILUMEN CATHETER

(71) Applicant: Cephea Valve Technologies, Inc., Santa Clara, CA (US)

(72) Inventors: Randolf von Oepen, Aptos, CA (US); Sean A. McNiven, Menlo Park, CA (US); Francisco Valencia, East Palo Alto, CA (US)

(73) Assignee: CEPHEA VALVE TECHNOLOGIES, INC., Santa Clara, CA (US)

( * ) Notice: Subject to any disclaimer, the term of this patent is extended or adjusted under 35 U.S.C. 154(b) by 35 days.

(21) Appl. No.: 15/662,093

(22) Filed: Jul. 27, 2017

(65) Prior Publication Data

US 2018/0056033 A1    Mar. 1, 2018

Related U.S. Application Data

(60) Provisional application No. 62/380,873, filed on Aug. 29, 2016.

(51) Int. Cl.
    *A61M 25/00*      (2006.01)
    *A61B 17/00*      (2006.01)
    (Continued)

(52) U.S. Cl.
    CPC ... *A61M 25/0026* (2013.01); *A61B 17/00234* (2013.01); *A61M 25/0032* (2013.01);
    (Continued)

(58) Field of Classification Search
    CPC .......... A61M 25/0026; A61M 25/0032; A61M 2025/0036; A61M 2025/004;
    (Continued)

(56) References Cited

U.S. PATENT DOCUMENTS 4,406,656 A    9/1983    Hattler et al.
4,728,319 A    3/1988    Masch
(Continued)

FOREIGN PATENT DOCUMENTS

CN    1469724      1/2004
CN    1688352 A    10/2005
(Continued)

OTHER PUBLICATIONS

Hironobu Takizawa et al. "Development of a Microfine Active Bending Catheter Equipped with MIF Tactile Sensors", Micro Electro Mechanical Systems, IEEE, Jan. 17, 1999, pp. 412-417.
(Continued)

*Primary Examiner* — Emily L Schmidt
*Assistant Examiner* — Leah J Swanson
(74) *Attorney, Agent, or Firm* — Workman Nydegger (57) ABSTRACT

An intravascular device delivery system includes an elongated member with a proximal end, a distal end, and a longitudinal axis therebetween. The elongated member includes a multilumen catheter having a catheter wall with a plurality of lumen in the catheter wall. The plurality of lumen extends from a proximal end of the elongated member to a distal end of the elongated member. A lumen ratio of the cross-sectional area of the plurality of lumen and the cross sectional area of the catheter wall is greater than 30%.

4 Claims, 4 Drawing Sheets

(51) Int. Cl.
*A61M 25/01* (2006.01)
*A61F 2/24* (2006.01)

(52) U.S. Cl.
CPC .... *A61M 25/0045* (2013.01); *A61M 25/0136* (2013.01); *A61M 25/0147* (2013.01); *A61B 2017/00243* (2013.01); *A61B 2017/00323* (2013.01); *A61F 2/2436* (2013.01); *A61F 2/2439* (2013.01); *A61M 25/005* (2013.01); *A61M 2025/004* (2013.01); *A61M 2025/0034* (2013.01); *A61M 2025/0035* (2013.01); *A61M 2025/0036* (2013.01); *A61M 2025/0046* (2013.01); *A61M 2025/0047* (2013.01)

(58) Field of Classification Search
CPC .......... A61M 25/0045; A61M 25/0147; A61M 25/0133; A61M 2025/0034; A61M 2025/0035; A61B 2017/00323; A61F 2/2439

See application file for complete search history.

(56) References Cited

U.S. PATENT DOCUMENTS

| | | | |
|---|---|---|---|
| 5,053,043 | A | 10/1991 | Gottesman et al. |
| 5,059,213 | A | 10/1991 | Chesterfield et al. |
| 5,078,722 | A | 1/1992 | Stevens |
| 5,078,723 | A | 1/1992 | Dance et al. |
| 5,236,450 | A | 8/1993 | Scott |
| 5,325,845 | A | 7/1994 | Adair |
| 5,345,945 | A | 9/1994 | Hodgson et al. |
| 5,387,219 | A | 2/1995 | Rappe |
| 5,415,664 | A | 5/1995 | Pinchuk |
| 5,472,423 | A | 12/1995 | Gronauer |
| 5,472,426 | A | 12/1995 | Bonati et al. |
| 5,571,085 | A | 11/1996 | Accisano, III |
| 5,662,606 | A | 9/1997 | Cimino et al. |
| 5,669,919 | A | 9/1997 | Sanders et al. |
| 5,769,812 | A | 6/1998 | Stevens et al. |
| 5,807,405 | A | 9/1998 | Vanney et al. |
| 5,820,591 | A | 10/1998 | Thompson et al. |
| 5,843,103 | A | 12/1998 | Wulfman |
| 5,855,601 | A | 1/1999 | Bessler et al. |
| 5,873,882 | A | 2/1999 | Straub et al. |
| 5,902,334 | A | 5/1999 | Dwyer et al. |
| 5,906,642 | A | 5/1999 | Caudillo et al. |
| 5,957,973 | A | 9/1999 | Quiachon et al. |
| 6,090,118 | A | 7/2000 | McGuckin, Jr. |
| 6,180,059 | B1 | 1/2001 | Divino, Jr. et al. |
| 6,228,110 | B1 | 5/2001 | Munsinger |
| 6,458,137 | B1 | 10/2002 | Klint |
| 6,517,550 | B1 | 2/2003 | Konya et al. |
| 6,695,836 | B1 | 2/2004 | DeMello et al. |
| 6,926,725 | B2 | 8/2005 | Cooke et al. |
| 7,172,617 | B2 | 2/2007 | Colgan et al. |
| 7,344,553 | B2 | 3/2008 | Opolski et al. |
| 7,666,204 | B2 | 2/2010 | Thornton et al. |
| 7,736,388 | B2 | 6/2010 | Goldfarb et al. |
| 7,837,727 | B2 | 11/2010 | Goetz et al. |
| 7,988,724 | B2 | 8/2011 | Salahieh et al. |
| 7,993,303 | B2 | 8/2011 | Von Oepen et al. |
| 8,157,852 | B2 | 4/2012 | Bloom et al. |
| 8,523,881 | B2 | 9/2013 | Cabiri et al. |
| 8,647,323 | B2 | 2/2014 | Guo et al. |
| 8,911,455 | B2 | 12/2014 | Quadri et al. |
| 8,926,588 | B2 * | 1/2015 | Berthiaume ............ A61F 2/966 |
| | | | 604/528 |
| 8,926,692 | B2 | 1/2015 | Dwork |
| 9,339,378 | B2 | 5/2016 | Quadri et al. |
| 9,370,423 | B2 | 6/2016 | Ryan |
| 9,393,112 | B2 | 7/2016 | Tuval et al. |
| 9,399,112 | B2 | 7/2016 | Shevgoor et al. |
| 9,668,859 | B2 | 6/2017 | Kheradvar et al. |
| 9,687,373 | B2 | 6/2017 | Vad |
| 9,693,862 | B2 | 7/2017 | Campbell et al. |
| 9,801,745 | B2 | 10/2017 | Wubbeling et al. |
| 10,111,671 | B2 | 10/2018 | Bodewadt |
| 10,117,760 | B2 | 11/2018 | Mangiardi |
| 10,376,673 | B2 | 8/2019 | Van Hoven et al. |
| 10,398,553 | B2 | 9/2019 | Kizuka |
| 10,470,902 | B2 | 11/2019 | Sheldon et al. |
| 2001/0002445 | A1 * | 5/2001 | Vesely .................. 623/2.11 |
| 2001/0047150 | A1 | 11/2001 | Chobotov |
| 2002/0013547 | A1 | 1/2002 | Paskar |
| 2004/0049207 | A1 | 3/2004 | Goldfarb et al. |
| 2004/0064179 | A1 | 4/2004 | Linder et al. |
| 2004/0116848 | A1 | 6/2004 | Gardeski et al. |
| 2004/0127849 | A1 | 7/2004 | Kantor |
| 2004/0133232 | A1 | 7/2004 | Rosenbluth et al. |
| 2004/0147826 | A1 | 7/2004 | Peterson |
| 2005/0038383 | A1 | 2/2005 | Kelley et al. |
| 2005/0085903 | A1 | 4/2005 | Lau |
| 2005/0137695 | A1 | 6/2005 | Salahieh et al. |
| 2005/0143809 | A1 | 6/2005 | Salahieh et al. |
| 2005/0256452 | A1 | 11/2005 | DeMarchi et al. |
| 2005/0259452 | A1 | 11/2005 | DeMarchi et al. |
| 2005/0283231 | A1 | 11/2005 | Haug et al. |
| 2005/0277874 | A1 | 12/2005 | Selkee |
| 2005/0277876 | A1 | 12/2005 | Hayden |
| 2005/0288768 | A1 | 12/2005 | Sowinski et al. |
| 2006/0135961 | A1 | 6/2006 | Rosenman et al. |
| 2007/0060997 | A1 | 3/2007 | de Boer |
| 2007/0156225 | A1 | 7/2007 | George et al. |
| 2007/0173757 | A1 | 7/2007 | Levine et al. |
| 2007/0197858 | A1 | 8/2007 | Goldfarb et al. |
| 2007/0203561 | A1 | 8/2007 | Forster et al. |
| 2007/0260225 | A1 | 11/2007 | Sakakine et al. |
| 2007/0270779 | A1 * | 11/2007 | Jacobs .............. A61M 25/0045 |
| | | | 604/525 |
| 2007/0299424 | A1 | 12/2007 | Cumming et al. |
| 2008/0103585 | A1 | 5/2008 | Monstadt et al. |
| 2008/0109065 | A1 | 5/2008 | Bowe |
| 2008/0188850 | A1 | 8/2008 | Mody et al. |
| 2008/0195126 | A1 | 8/2008 | Solem |
| 2009/0036768 | A1 | 2/2009 | Seehusen et al. |
| 2009/0069885 | A1 | 3/2009 | Randert et al. |
| 2009/0099554 | A1 | 4/2009 | Forster et al. |
| 2009/0163934 | A1 | 6/2009 | Raschdorf, Jr. et al. |
| 2009/0182407 | A1 | 7/2009 | Leanna et al. |
| 2009/0204005 | A1 | 8/2009 | Keast et al. |
| 2009/0240326 | A1 | 9/2009 | Wilson et al. |
| 2009/0276039 | A1 | 11/2009 | Meretei |
| 2009/0281619 | A1 | 11/2009 | Le et al. |
| 2010/0004739 | A1 | 1/2010 | Vesely |
| 2010/0044410 | A1 | 2/2010 | Argentine et al. |
| 2010/0059173 | A1 | 3/2010 | Kampa et al. |
| 2010/0070009 | A1 * | 3/2010 | Barker .................. H01R 31/02 |
| | | | 607/117 |
| 2010/0217261 | A1 | 8/2010 | Watson |
| 2010/0249894 | A1 | 9/2010 | Oba et al. |
| 2010/0331776 | A1 | 12/2010 | Salahieh et al. |
| 2011/0112630 | A1 | 5/2011 | Groothuis et al. |
| 2011/0166566 | A1 | 7/2011 | Gabriel |
| 2011/0166649 | A1 | 7/2011 | Gross et al. |
| 2011/0202128 | A1 | 8/2011 | Duffy |
| 2011/0257718 | A1 | 10/2011 | Argentine |
| 2011/0307049 | A1 | 12/2011 | Kao |
| 2012/0022640 | A1 | 1/2012 | Gross et al. |
| 2012/0065464 | A1 * | 3/2012 | Ellis et al. .................. 600/104 |
| 2012/0109078 | A1 | 5/2012 | Schaeffer |
| 2012/0172915 | A1 | 7/2012 | Fifer et al. |
| 2012/0316639 | A1 | 12/2012 | Kleinschrodt |
| 2012/0330348 | A1 | 12/2012 | Strauss et al. |
| 2012/0330408 | A1 | 12/2012 | Hillukka et al. |
| 2013/0030514 | A1 | 1/2013 | Kasprzak et al. |
| 2013/0041314 | A1 | 2/2013 | Dillon |
| 2013/0066342 | A1 | 3/2013 | Dell et al. |
| 2013/0103001 | A1 | 4/2013 | BenMaamer et al. |
| 2013/0109910 | A1 | 5/2013 | Alexander et al. |
| 2013/0131775 | A1 | 5/2013 | Hadley et al. |
| 2013/0289696 | A1 | 10/2013 | Maggard et al. |
| 2014/0107693 | A1 | 4/2014 | Plassman |
| 2014/0114390 | A1 | 4/2014 | Tobis et al. |

(56) References Cited

U.S. PATENT DOCUMENTS

| | | |
|---|---|---|
| 2014/0142688 A1 | 5/2014 | Duffy et al. |
| 2014/0148889 A1 | 5/2014 | Deshmukh et al. |
| 2014/0180124 A1 | 6/2014 | Whiseant et al. |
| 2014/0200649 A1 | 7/2014 | Essinger et al. |
| 2014/0228871 A1 | 8/2014 | Cohen et al. |
| 2014/0276966 A1 | 9/2014 | Ranucci et al. |
| 2014/0324164 A1 | 10/2014 | Gross et al. |
| 2014/0336744 A1 | 11/2014 | Tani et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0088189 A1 | 3/2015 | Paul, Jr. |
| 2015/0112430 A1 | 4/2015 | Creaven et al. |
| 2015/0272759 A1 | 10/2015 | Argentine |
| 2015/0306806 A1 | 10/2015 | Dando et al. |
| 2016/0045311 A1 | 2/2016 | McCann et al. |
| 2016/0074163 A1 | 3/2016 | Yang et al. |
| 2016/0113765 A1 | 4/2016 | Ganesan et al. |
| 2016/0143661 A1 | 5/2016 | Wood et al. |
| 2017/0035566 A1* | 2/2017 | Krone .............. A61M 25/0026 |
| 2017/0042678 A1 | 2/2017 | Ganesan et al. |
| 2017/0080186 A1 | 3/2017 | Salahieh et al. |
| 2017/0232238 A1 | 8/2017 | Biller et al. |
| 2018/0028177 A1 | 2/2018 | von Oepen et al. |
| 2018/0028215 A1 | 2/2018 | Cohen |
| 2018/0028305 A1 | 2/2018 | von Oepen et al. |
| 2018/0028779 A1 | 2/2018 | von Oepen et al. |
| 2018/0028787 A1 | 2/2018 | McNiven et al. |
| 2018/0055636 A1 | 3/2018 | Valencia et al. |
| 2018/0055637 A1 | 3/2018 | von Oepen et al. |
| 2018/0056043 A1 | 3/2018 | von Oepen et al. |
| 2018/0071098 A1 | 3/2018 | Alon |
| 2018/0092744 A1 | 4/2018 | von Oepen et al. |
| 2018/0126119 A1 | 5/2018 | McNiven et al. |
| 2018/0132837 A1 | 5/2018 | Mathena et al. |
| 2018/0133454 A1 | 5/2018 | von Oepen et al. |
| 2018/0360457 A1 | 12/2018 | Ellis et al. |
| 2019/0030285 A1 | 1/2019 | Prabhu et al. |
| 2019/0274831 A1 | 9/2019 | Prabhu |
| 2020/0155804 A1 | 5/2020 | von Oepen et al. |
| 2020/0230352 A1 | 7/2020 | Mcniven et al. |
| 2020/0230354 A1 | 7/2020 | Von Oepen et al. |

FOREIGN PATENT DOCUMENTS

| | | |
|---|---|---|
| CN | 1961983 A | 5/2007 |
| CN | 101247847 A | 8/2008 |
| CN | 101426452 A | 5/2009 |
| CN | 101506538 A | 8/2009 |
| CN | 102159277 A | 8/2011 |
| CN | 102258402 A | 11/2011 |
| CN | 102481433 A | 5/2012 |
| CN | 102548505 A | 7/2012 |
| CN | 102770080 | 11/2012 |
| CN | 102933161 A | 2/2013 |
| CN | 103517689 A | 1/2014 |
| CN | 103702635 A | 4/2014 |
| CN | 103841899 | 6/2014 |
| CN | 103957993 A | 7/2014 |
| CN | 104203329 A | 12/2014 |
| CN | 104812439 A | 7/2015 |
| CN | 105246434 A | 1/2016 |
| CN | 105899167 A | 8/2016 |
| EP | 1980288 | 4/2008 |
| EP | 1980288 | 10/2008 |
| EP | 2537487 | 12/2012 |
| EP | 2702965 | 3/2014 |
| EP | 3009103 | 4/2016 |
| JP | 2003062072 | 3/2003 |
| JP | 2006528911 | 12/2006 |
| JP | 2013516244 | 5/2013 |
| WO | WO 2001051114 | 7/2001 |
| WO | WO 2007044285 | 4/2007 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | 2012/057983 A1 | 5/2012 |
| WO | WO 2012151396 | 11/2012 |
| WO | 2013/126529 A2 | 8/2013 |
| WO | WO 2014064694 | 5/2014 |
| WO | WO 2014121280 | 8/2014 |
| WO | WO 2014128705 | 8/2014 |
| WO | WO 2015191938 | 12/2015 |
| WO | WO 2016022797 | 2/2016 |
| WO | WO 2016112085 | 7/2016 |
| WO | WO 2016144708 | 9/2016 |
| WO | WO 2016150806 | 9/2016 |
| WO | WO 2016183526 | 11/2016 |
| WO | 20171023534 A2 | 2/2017 |
| WO | WO 2018023038 | 2/2018 |
| WO | WO 2018023043 | 2/2018 |
| WO | WO 2018023044 | 2/2018 |
| WO | WO 2018023045 | 2/2018 |
| WO | WO 2018023052 | 2/2018 |
| WO | WO 2018044446 | 3/2018 |
| WO | WO 2018044447 | 3/2018 |
| WO | WO 2018044448 | 3/2018 |
| WO | WO 2018044449 | 3/2018 |
| WO | WO 2018067788 | 4/2018 |

OTHER PUBLICATIONS

U.S. Appl. No. 15/662,001, dated Jun. 20, 2019 Office Action.
U.S. Appl. No. 15/662,001, dated Oct. 4, 2019, Office Action.
U.S. Appl. No. 15/662,001, dated Dec. 18, 2019, Notice of Allowance.
U.S. Appl. No. 15/66,2013, dated Jun. 13, 2019, Office Action.
U.S. Appl. No. 15/662,013, dated Oct. 10, 2019, Office Action.
U.S. Appl. No. 15/662,013, dated Dec. 5, 2019, Advisory Action.
U.S. Appl. No. 15/662,066, dated Jul. 11, 2019, Office Action.
U.S. Appl. No. 15/662,066, dated Dec. 16, 2019, Office Action.
U.S. Appl. No. 15/662,066, dated Feb. 27, 2020, Advisory Action.
U.S. Appl. No. 15/662,142, dated Dec. 20, 2019 Advisory Action.
U.S. Appl. No. 15/662,076, dated Oct. 8, 2019, Notice of Allowance.
U.S. Appl. No. 15/662,076, dated Jan. 31, 2020, Notice of Allowance.
U.S. Appl. No. 15/662,089, dated Oct. 7, 2019, Office Action.
U.S. Appl. No. 15/662,089, dated Jan. 10, 2020, Office Action.
U.S. Appl. No. 15/662,008, dated Sep. 13, 2019, Office Action.
U.S. Appl. No. 15/662,008, dated Jan. 31, 2020, Notice of Allowance.
U.S. Appl. No. 15/662,098, dated Jul. 5, 2019, Office Action.
U.S. Appl. No. 15/662,098, dated Jan. 27, 2020, Office Action.
U.S. Appl. No. 15/724,499, dated Jul. 15, 2019, Notice of Allowance.
U.S. Appl. No. 15/724,499, dated Aug. 27, 2019, Supplemental Notice of Allowance.
U.S. Appl. No. 15/724,499, dated Nov. 22, 2019, Supplemental Notice of Allowance.
U.S. Appl. No. 15/662,142, dated Apr. 17, 2020, Office Action.
U.S. Appl. No. 15/662,001, dated Mar. 24, 2020, Notice of Allowance.
U.S. Appl. No. 15/662,098, dated Mar. 23, 2020, Advisory Action.
U.S. Appl. No. 15/724,499, dated Mar. 25, 2020, Office Action.
U.S. Appl. No. 15/662,013, dated May 7, 2020, Notice of Allowance.
U.S. Appl. No. 15/662,098, dated Apr. 30, 2020, OA.
U.S. Appl. No. 15/662,066, dated May 21, 2020, Office Action.
U.S. Appl. No. 15/662,089, dated Jun. 11, 2020, Office Action.
Notice of Allowance received for U.S. Appl. No. 15/724,499, dated Jul. 1, 2020.

* cited by examiner

MULTILUMEN CATHETER

CROSS-REFERENCE TO RELATED APPLICATIONS

This application claims the benefit of and priority to U.S. Provisional Patent Application Ser. No. 62/380,873 filed on Aug. 29, 2016 and entitled "Multilumen Catheter," which application is expressly incorporated herein by reference in its entirety.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

BRIEF SUMMARY OF THE DISCLOSURE

In an embodiment, an intravascular device delivery system includes an elongated member with a proximal end, a distal end, and a longitudinal axis therebetween. The elongated member includes a multilumen catheter having a catheter wall with a plurality of lumen in the catheter wall. The plurality of lumen extends from a proximal end of the elongated member to a distal end of the elongated member. A lumen ratio of the cross-sectional area of the plurality of lumen and the cross sectional area of the catheter wall is greater than 30%.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular system. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 3 may be combinable with any element of an embodiment described in FIG. 4, and any element described in relation to an embodiment described in FIG. 5 may be combinable with any element of an embodiment depicted in FIG. 2.

An intravascular device delivery system may include a flexible elongated member that has a distal end and a proximal end. A handle may be connected to a proximal end of the elongated member to allow a user, such as a medical professional and/or clinician, to control one or more movements of the elongated member. An intravascular device may be positioned at and/or connected to the distal end of the elongated member.

In some embodiments, the intravascular device delivery system may be configured to delivery an intravascular device that is controlled and/or retained in the elongated member with a plurality of tension members. The tension members may extend from the handle, through at least a portion of the elongated member in a longitudinal direction to the intravascular device. In some embodiments, the tension members connect to the intravascular device to retain the intravascular device in the elongated member during movement of the intravascular device delivery system through the patient's anatomy. In other embodiments, the tension members connect to the intravascular device to actuate one or more moveable and/or deformable portions of the intravascular device, such as a clip used to secure the intravascular device at a target location in the body.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

Figure 1:
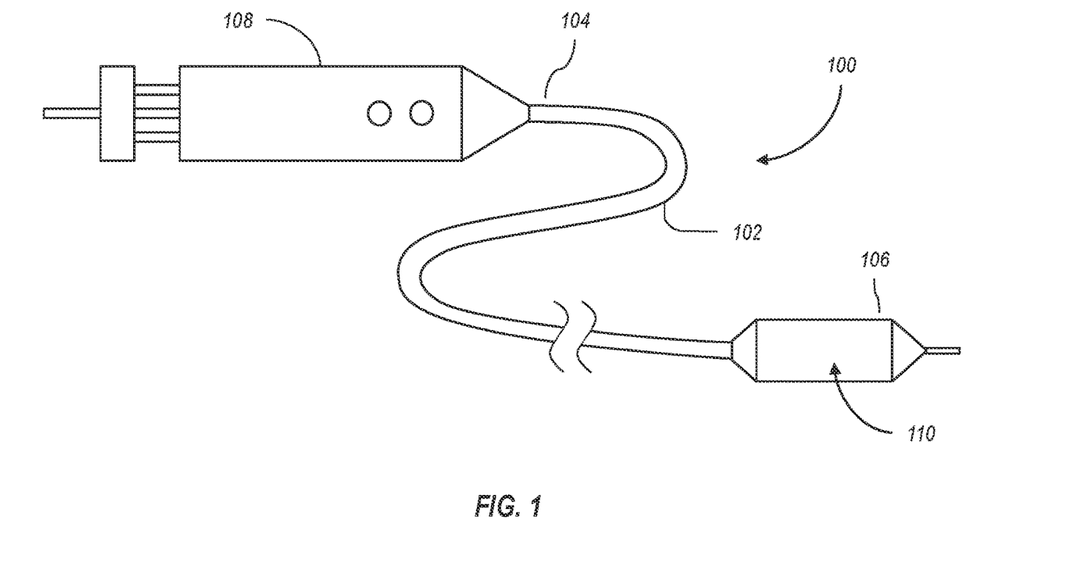
FIG. 1 is a schematic embodiment of an intravascular device delivery system, according to the present disclosure.

FIG. 1 illustrates a schematic representation of an intravascular device delivery system 100. The system 100 may include an elongated member 102 having a proximal end 104 and a distal end 106. One or more handles 108 may be connected to the proximal end 104 of the elongated member 102. An intravascular device 110 may be positioned at and/or connected to the distal end 106.

The elongated member 102 may be flexible, allowing the elongated member 102 to traverse a patient's tortuous vasculature or other anatomy. In some embodiments, the elongated member 102 may deliver the intravascular device 110 to a target location in the patient's body, such as delivering a heart valve repair device to the heart. In other embodiments, the system 100 and elongated member 102 may be provided without an intravascular device 110 at the distal end 106 such that the system may recapture, reposition, or otherwise move an intravascular device previously positioned in the patient's body.

The elongated member 102 of the system 100 may include one or more elements therein. An element of the elongated member 102 may include a catheter, a guidewire, a sheath, a drive cable, other tubular and/or solid element, or combinations thereof. In some embodiments an element of the elongated member 102 may extend an entire length of the elongated member 102 from a proximal end 104 to a distal end 106 of the elongated member 102. In other embodiments, an element of the elongated member 102 may have a length less than the entire length of the elongated member 102. For example, an element may provide support to the elongated member 102 from the proximal end 104 toward the distal end 106 without continuing the entire length to the distal end 106.

Figure 2:
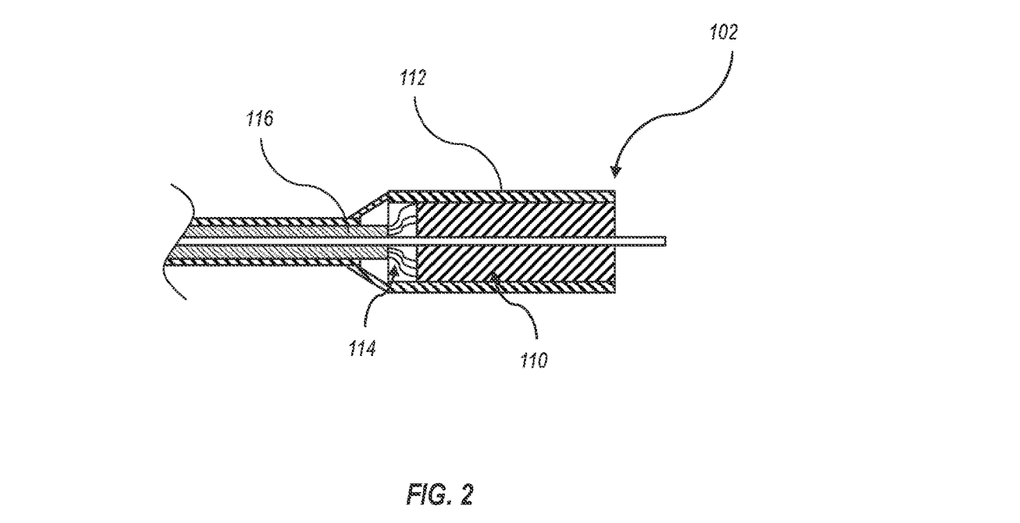
FIG. 2 is a detail perspective view of an embodiment of a distal end of the intravascular device delivery system of FIG. 1, according to the present disclosure.

FIG. 2 illustrates a schematic detail cross-sectional side view of an embodiment of the distal end 106 of the elongated member 102 of FIG. 1. The intravascular device 110 is positioned radially within an outer sleeve 112 of the elongated member 102. The intravascular device 110 is carried by the elongated member 102 through the patient's anatomy to the target location in the body. At the target location, the intravascular device 110 may be urged in a distal longitudinal direction such that the intravascular device 110 is no longer radially constrained by the outer sleeve 112. In other embodiments, the outer sleeve 112 may be retracted in a proximal longitudinal direction to allow the intravascular device 110 to deploy radially. In yet other embodiments, the intravascular device 110 is deployed through a combination of the intravascular device 110 moving relative to the elongated member 102 and the outer sleeve 112 moving relative to the remainder of the elongated member 102.

Prior to and/or during deployment of the intravascular device 110, the intravascular device 110 may be retained within the outer sleeve 112 (e.g., the distal longitudinal movement of the intravascular device 110 may be limited) by a plurality of tension members 114 connected to the intravascular device 110. The tension members 114 may be directed to the intravascular device 110 through a multilumen catheter 116 and connect to both a handle and to the intravascular device 110 to transmit tension from the handle to the intravascular device 110. In some embodiments, the tension members 114 are also used to collapse the intravascular device 110 during loading into the outer sleeve 112. During loading, high forces (i.e., up to 100 pounds of force) may be generated and additional tension members 114 may distribute the force more to reduce the likelihood of any one of the tension members 114 failing.

Figure 3:
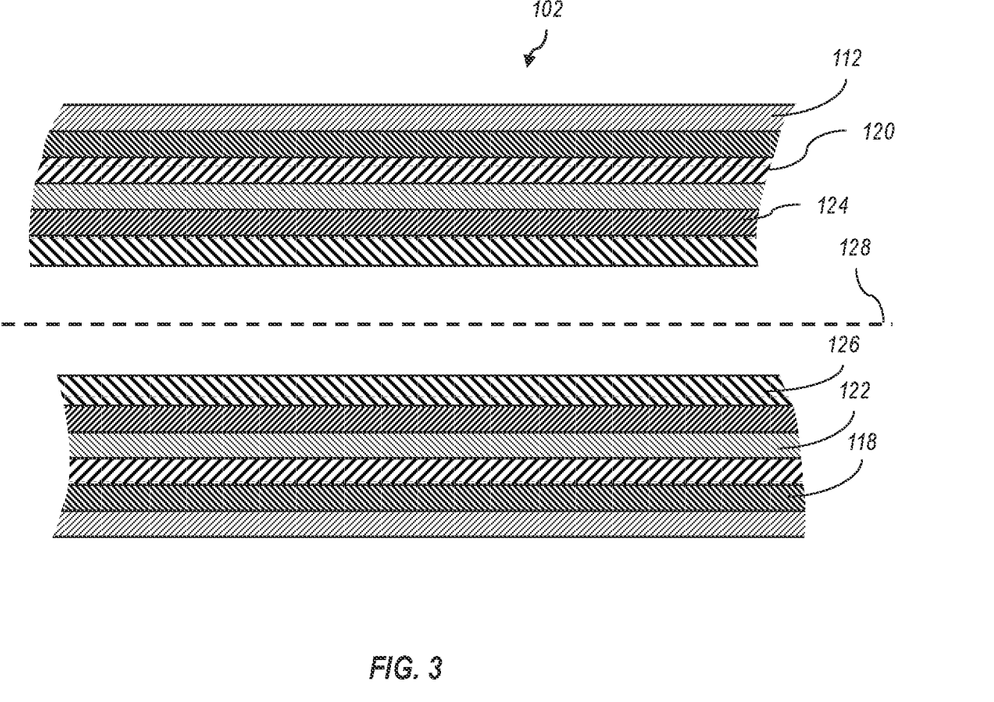
FIG. 3 is a cross-sectional side view of the embodiment of an elongated member of the intravascular device delivery system of FIG. 1, according to the present disclosure.

FIG. 3 is a side partial cutaway view of part of an embodiment of the elongated member 102 of the intravascular device delivery system 100 of FIG. 1. In some embodiments, the elongated member 102 may include an outer sleeve 112, a steerable guide catheter 118, a steerable catheter 120, a compression coil 122, and an inner catheter 124. Any of the steerable guide catheter 118, steerable catheter 120, and the inner catheter 124 in the elongated member 102 may be a multilumen catheter, according to the present invention. The guidewire lumen 126 may be positioned radially within the inner catheter 124 and parallel to a longitudinal axis 128 of the elongated member 102. One or more of the elements of the elongated member 102 may be longitudinally moveable relative to one another. In some embodiments, at least one of the elements of the elongated member is longitudinally fixed relative to another. For example, the inner catheter 124 and compression coil 122 may be longitudinally fixed relative to one another at a distal end of the inner catheter 124 and compression coil 122.

Additionally, one or more elements of the elongated member 102 may be rotationally moveable relative to one another. In some embodiments, at least one of the elements of the elongated member is rotationally fixed relative to another. For example, the outer sleeve 112 and steerable guide catheter 118 may be rotationally fixed relative to one another at an intermediate position between the proximal end and the distal end of the outer sleeve 112.

The multilumen catheter will, during delivery of the intravascular device through the vasculature of the patient, deflect. The length of the tension members relative to one another will change during deflection. For example, tension members which are positioned proximal the inside of a curve will have a shorter distance than those running on the outside of a curve. It may be desirable to keep the diameter of the multilumen catheter as small as possible. A small diameter multilumen catheter may position the tension members 114 closer to the longitudinal axis 128 of the elongated member 102, thereby reducing the relative displacement during deflection.

Figure 4:
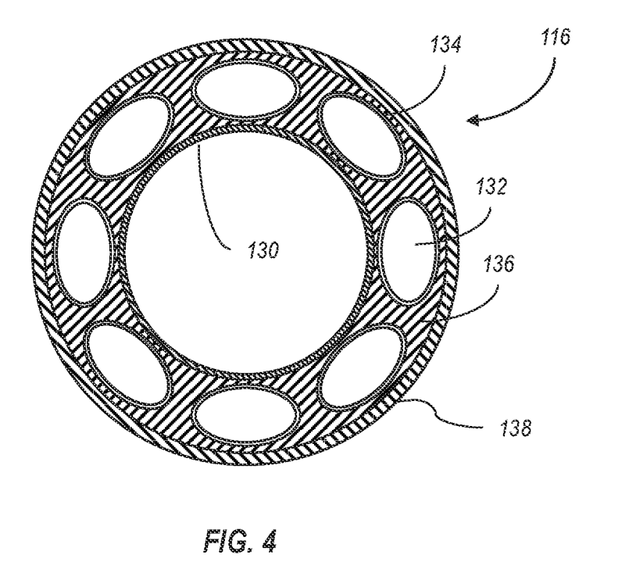
FIG. 4 is a detail transverse cross-sectional view of the embodiment of a multilumen catheter of the intravascular device delivery system of FIG. 1, according to the present disclosure.

FIG. 4 illustrates a transverse cross-sectional view of a multilumen catheter 116 according to the present disclosure. The multilumen catheter 116 includes an inner liner 130. The inner liner 130 may include polytetrafluoroethylene (PTFE) or any other lubricous material. A plurality of lumen 132 formed of lubricous tubing (i.e. Polyimide) are placed around the inner liner 130 (in this case 8 lumens). The lumens 132 are hold together by a thin braid 134 or coil over the lumens and are covered by a polymeric jacket to form the wall 136 of the multilumen catheter 116.

The thin walled lumen 132 placed in the catheter wall 136 may deform during the delivery process and the deflection of the elongated member. The below calculations shows that the lumen ratio of open lumen 132 to catheter wall 136 may be greater than 50%. The calculation is based on a catheter wall without the inner liner 130, the braid 134, and an outer jacket 138. Adding the inner liner 130, the braid 134, and the outer jacket 138 into the calculation may yield a lumen ratio more than 40%. Tension members may be positioned within the lumen 132 to convey and direct the tension members through the elongated member between the handle and the intravascular device.

Figure 5:
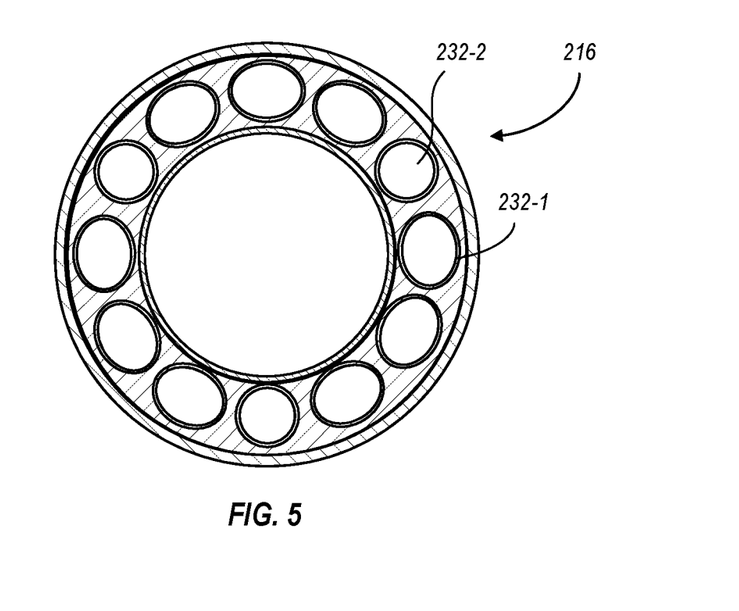
FIG. 5 is a detail transverse cross-sectional side view of another embodiment of a multilumen catheter of an intravascular device delivery system, according to the present disclosure.

FIG. 5 illustrates an embodiment of a multilumen catheter 216 with nine elliptical lumen 232-1 and three round lumen 232-2 for a total of twelve lumen. An outer diameter of the catheter wall is about 1.5 times an internal diameter of the catheter wall. Calculations for the multilumen catheter 216 shown in FIG. 5 are set forth in Table 1 below:

TABLE 1

|  |  | a | b | d | A | C |
|---|---|---|---|---|---|---|
| circumferences ellipse | $C = 2\pi\sqrt{\dfrac{a^2 + b^2}{2}}$ | 0.006 | 0.007875 |  |  | 0.0439 |
| circumferences cycle | $C = \pi d$ |  |  | 0.014 |  | 0.0439 |
| cross section ellipse | $A = \pi a b$ |  |  |  | 0.000148 |  |
| cross section cycle | $A = \pi \dfrac{d^2}{4}$ |  |  |  | 0.000154 |  |

| Total Lumen | 3 round | 9 ellipse | Area total |
|---|---|---|---|
| Area | 0.000339282 | 0.001336 | 0.001675 |
| Wall Cross Section without liner, braid and jacket | ID 0.056 | OD 0.084 | Area 0.003079 |
| Ratio Lumen/Wall without liner, braid and jacket |  |  | 54.41% |
| Wall Cross Section with liner, braid and jacket | 0.054 | 0.09 | 0.004071 |
| Ratio Lumen/wall with liner, braid and jacket |  |  | 41.15% |

Figure 6:
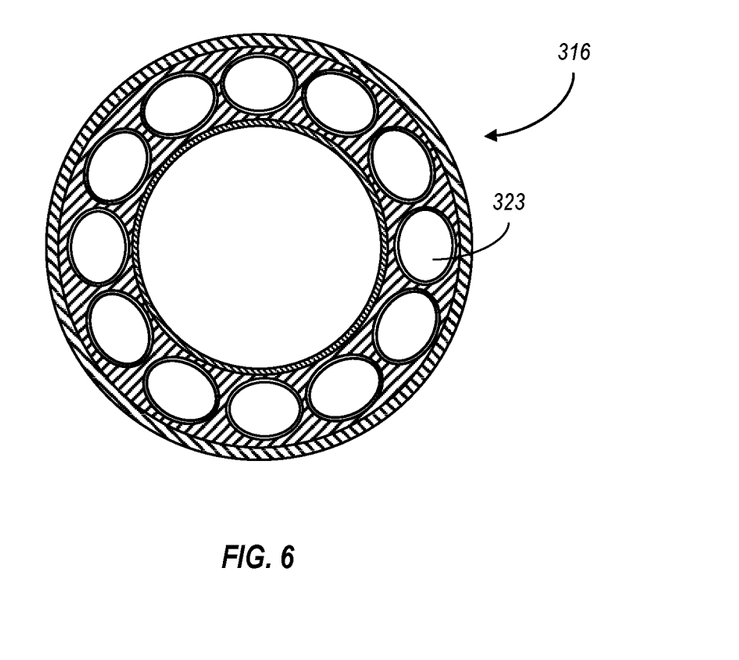
FIG. 6 is detail transverse cross-sectional side view of another embodiment of a multilumen catheter of an intravascular device delivery system, according to the present disclosure.

FIG. 6 illustrates another embodiment of a multilumen catheter 316 with twelve elliptical lumen 323. Calculations for the multilumen catheter 316 shown in FIG. 6 are set forth in Table 2 below:

TABLE 2

|  |  | a | b | d | A | C |
|---|---|---|---|---|---|---|
| circumferences ellipse | $C = 2\pi\sqrt{\dfrac{a^2 + b^2}{2}}$ | 0.006 | 0.007875 |  |  | 0.0439 |

TABLE 2-continued

| | | | | |
|---|---|---|---|---|
| circumferences cycle | $C = \pi d$ | | 0.014 | 0.0439 |
| cross section ellipse | $A = \pi a b$ | | | 0.000148 |
| cross section cycle | $A = \pi \dfrac{d^2}{4}$ | | | 0.000154 |
| Total Lumen | | | 12 ellipse | Area total |
| Area | | | 0.001781 | 0.001781 |
| Wall Cross Section without liner, braid and jacket | | ID | OD | Area |
| | | 0.056 | 0.084 | 0.003079 |
| Ratio Lumen/Wall without liner, braid and jacket | | | | 57.86% |
| Wall Cross Section with liner, braid and jacket | | 0.054 | 0.09 | 0.004071 |
| Ratio Lumen/wall with liner, braid and jacket | | | | 43.75% |

Figure 7:
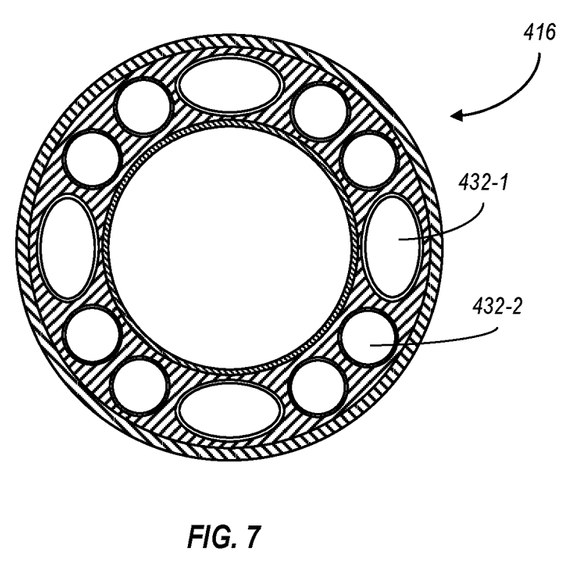
FIG. 7 is detail transverse cross-sectional side view of yet another embodiment of a multilumen catheter of an intravascular device delivery system, according to the present disclosure.

FIG. 7 illustrates yet another embodiment of a multilumen catheter 416 with a four elliptical lumen 432-1 and eight round lumen 432-2 for a total of twelve lumen.

In some embodiments, an intravascular device delivery system according to the present disclosure may allow delivery of larger intravascular devices and/or through smaller bodily conduits. The intravascular device delivery system may allow for new and/or improved procedures with less risk to the patient and greater ease of operation to the medical professional.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An intravascular device delivery system, the system comprising:
    an elongated member with a proximal end, a distal end, and a longitudinal axis therebetween, the elongated member comprising including:
    an outer sleeve having an enlarged distal end forming a cavity to receive an intravascular device, the enlarged distal end having a diameter greater than a diameter of the elongated member proximal a proximal end of the enlarged distal end; and
    a multilumen catheter having a distal end disposed within the cavity of the enlarged distal end and distal a transition from the enlarged distal end to a portion of the elongated member proximal the proximal end of the enlarged distal end, the multilumen catheter consisting of:
        an outer jacket forming an outer surface of the multilumen catheter;
        a lubricious inner liner forming a guidewire lumen; and
        a catheter wall extending between and contacting the outer jacket and the inner liner, the catheter wall being formed of a plurality of lubricious tubes held together by a thin supporting member covered by a polymeric jacket, the thin supporting member being a braid or coil, the plurality of tubes including at least one elliptical lumen tube having an elliptical cross-section and at least one circular lumen tube with a circular cross-section, the plurality of tubes extend from a proximal end of the elongated member to the distal end of the multilumen catheter within the cavity, wherein a lumen ratio of a cross-sectional area of a plurality of lumens formed by the plurality of tubes and a cross sectional area of the catheter wall, in a direction perpendicular to a longitudinal axis of the catheter, is greater than 30%.

2. The system of claim 1, wherein the lumen ratio is greater than 40%.

3. The system of claim 2, wherein the lumen ratio is greater than 50%.

4. An intravascular device delivery system, the system comprising:

an elongated member with a proximal end, a distal end, and a longitudinal axis therebetween, the elongated member comprising:

an outer sleeve having an enlarged distal end forming a cavity to receive an intravascular device, the enlarged distal end having a diameter greater than a diameter of the elongated member proximal a proximal end of the enlarged distal end;

a compression coil disposed within the outer sleeve;

a multilumen catheter disposed within the compression coil, the multilumen catheter consisting of:

an outer jacket forming an outer surface of the multilumen catheter;

a lubricious inner liner forming a guidewire lumen; and a catheter wall extending between and contacting the outer jacket and the inner liner, the catheter wall consisting of twelve lubricious tubes held together by a thin supporting member covered by a polymeric jacket, the thin supporting member being a braid or coil, the tubes including at least one elliptical lumen tube having an elliptical cross-section and at least one circular lumen tube with a circular cross-section, the tubes extend from a proximal end of the elongated member to a distal end of the elongated member, wherein a lumen ratio of a cross-sectional area of a plurality of lumens formed by the tubes and a cross sectional area of the catheter wall, in a direction perpendicular to a longitudinal axis of the catheter, is greater than 50% with an outer diameter of the catheter wall being about 1.5 times an internal diameter of the catheter wall.

* * * * *